United States Patent
Suzuki et al.

(10) Patent No.: US 6,242,635 B1
(45) Date of Patent: Jun. 5, 2001

(54) PROCESS FOR PRODUCING PROPIONIC ACID DERIVATIVES

(75) Inventors: Takayuki Suzuki; Takayuki Hamada; Kunisuke Izawa, all of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/156,900

(22) Filed: Sep. 18, 1998

(30) Foreign Application Priority Data

Oct. 3, 1997 (JP) ................................................ 9-288041

(51) Int. Cl.$^7$ ........................ C07C 67/00; C07C 69/612; C07C 69/66
(52) U.S. Cl. ................ 560/55; 560/56; 560/60; 562/465; 562/466; 562/470
(58) Field of Search ................. 560/55, 56, 60; 562/466, 470, 465

(56) References Cited

U.S. PATENT DOCUMENTS 4,939,288   7/1990   Talley ..................................... 560/81

OTHER PUBLICATIONS

Ohshima et al., Synthesis of . . . Asymmetric Hydrogenation, Enatiomer, vol. 3, pp. 191–195, 1998.*

Paul H. Mason, et al., Tetrahedron, vol. 50, No. 41, pp. 12001–12008, "Some Mechanistic and Synthetic Aspects of the Dabco Catalysed Rearrangement of Allylic Esters", Oct. 10, 1994.

Sara Rafel, et al., Journal of Organic Chemistry, vol. 62, No. 5, pp. 1521–1522, "An Unexpected Rate Acceleration–Practical Improvements in the Baylis–Hillman Reaction", Mar. 7, 1997.

* cited by examiner

Primary Examiner—Johann Richter
(74) Attorney, Agent, or Firm—Oblon, Spivak, McClelland, Maier & Neustadt, P.C.

(57) ABSTRACT

A process for producing a 2-aralkyl-3-hydroxypropionic acid (or its ester), comprising the steps of: reacting a 3-hydroxy-2-methylene-3-arylpropionic acid ester, easily obtained by the reaction of an arylaldehyde with an acrylic acid ester, with an acid anhydride to form a 2-aralkylidene-3-acyloxypropionic acid ester; subjecting the same to hydrolysis or alcoholysis; and reducing the resulting 2-aralkylidene-3-hydroxypropionic acid or its ester. The reduction step may be conducted in the presence of a base.

7 Claims, No Drawings

PROCESS FOR PRODUCING PROPIONIC ACID DERIVATIVES

BACKGROUND OF THE INVENTION

Field of the Invention

The present invention relates to a novel process for producing a propionic acid derivative. More specifically, the present invention relates to a novel process for producing a 2-aralkyl-3-hydroxypropionic acid or its ester. The 2-aralkyl-3-hydroxypropionic acid can produce the optically active substance thereof through optical resolution with a resolving agent or an enzyme. This is convertible into an intermediate which is extremely important as a constituent of a lenin inhibitor (refer to J. Med. Chem. 1988, vol. 31, 1839 and WO 9116031), an enkephalinase inhibitor (refer to Japanese Patent Kokai Publication Nos. JP-A-2-161 and JP-A-8-59,606) or a protease inhibitor (refer to Japanese Patent Kohyou Publication No. JP-A-9-505,284).

DESCRIPTION OF THE RELATED ART

As a method of producing a 2-aralkyl-3-hydroxypropionic acid, a method has been so far known which comprises treating Meldrum's acid as a starting material with benzaldehyde and a borane.triethylamine complex to form benzyl-Meldrum's acid, then reacting the same with benzyl alcohol to form α-benzylmalonic acid monobenzyl ester, and reducing the same with lithium aluminum hydride to produce 2-benzyl-3-hydroxypropionic acid (refer to WO 9209297). This method is however problematic in that the reducing agent (borane.triethylamine complex and lithium aluminum hydride) of Meldrum's acid is expensive, the borane.triethylamine complex is toxic, and the lithium aluminum hydride reduction reaction requires a low-temperature reaction and is also industrially dangerous. Accordingly, this method is not said to be an industrial method. Further, a method has been known which comprises treating hydrocinnamic acid with lithium diisopropylamide and then reacting the resulting substance with a formaldehyde gas to form 2-benzyl-3-hydroxypropionic acid (refer to J. Med. Chem., 1992, vol. 35, 1472). However, this method is also industrially problematic in that expensive lithium diisopropylamide is used, the formaldehyde gas is highly toxic, a low-temperature reaction is required and the yield is low. Still further, a method has been known which comprises subjecting β-propiolactone to a ring-opening reaction with methanol in the presence of triethylamine to form 3-hydroxypropionic acid methyl ester, and then α-benzylating the same with lithium diisopropylamide and with benzyl bromide to obtain 2-benzyl-3-hydroxypropionic acid methyl ester (refer to J. Med. Chem., 1993, vol. 36, 4015). However, this method is also problematic in that starting β-propiolactone and lithium diisopropylamide are expensive, a low-temperature reaction is required and the yield is low. Furthermore, a method has been known which comprises reacting α-hydroxymethylacrylic acid ethyl ester with diphenyl copper magnesium bromide for a conjugate addition of a phenyl group to obtain 2-benzyl-3-hydroxypropionic acid ethyl ester (refer to J. Organometallic Chem., 308, 1986, C27). However, this reaction is also industrially problematic in that the copper (I) reagent is expensive and a low-temperature reaction is required.

1. Problems to be Solved by the Invention

The many problems to be solved for the related arts are as mentioned above, and in the course of the completion of the present invention, the above-mentioned problems have been also found by the present inventors.

The present invention is to provide a process for producing a 2-aralkyl-3-hydroxypropionic acid, particularly 2-arylmethyl-3-hydroxypropionic acid (including its ester) industrially safely and easily.

SUMMARY OF THE INVENTION

The present inventors have assiduously conducted investigations to solve the above-mentioned problems, and have consequently found that a 2-aralkyl-3-hydroxypropionic acid or its ester can be produced quite easily using an arylaldehyde and an acrylic acid ester which can be obtained industrially easily as starting materials through a short synthesis route including four simple reaction steps, namely, a step of a reaction of both starting materials, a step of an acid anhydride treatment, a step of hydrolysis (or alcoholysis) and a step of reduction. In more detail, they have found that a 2-aralkyl-3-hydroxypropionic acid (including its ester) can be produced by reacting both of the above-mentioned starting materials to easily form a 3-hydroxy-2-methylene-3-arylpropionic acid ester, then reacting this ester with an acid anhydride in the presence of an acid to form a 2-aralkylidene-3-acyloxypropionic acid ester, subjecting this ester to hydrolysis or alcoholysis, and reducing the resulting 2-aralkylidene-3-hydroxypropionic acid or its ester. This finding has led to the completion of the present invention (first invention).

Further, they have assiduously conducted investigations on a method of reducing the above-mentioned 2-aralkylidene-3-hydroxypropionic acid in a high yield as another problem, and have consequently found that this problem can be solved by the presence of a base in the reducing reaction thereof. This finding has led to the completion of the present invention (second invention).

That is, the first invention is characterized by the synthesis route including the following four simple steps.

The first step is a step of reacting an arylaldehyde represented by formula (I)

$$R^1CHO \quad (I)$$

wherein $R^1$ represents an aryl group with an acrylic acid ester represented by formula (II)

(II)

wherein $R^2$ represents a hydrocarbon group to form a 3-hydroxy-2-methylene-3-arylpropionic acid ester represented by formula (III)

(III)

wherein $R^1$ and $R^2$ are as defined above.

The second step is a step of reacting a 3-hydroxy-2-methylene-3-arylpropionic acid ester of formula (III) with an acid anhydride to produce a 2-aralkylidene-3-acyloxypropionic acid ester represented by formula (IV)

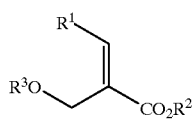

wherein $R^1$ and $R^2$ are as defined above, and $R^3$ represents an acyl group.

The third step is a step of subjecting the 2-aralkylidene-3-acyloxypropionic acid ester of formula (IV) to hydrolysis or alcoholysis to produce a 2-arylmethylene-3-hydroxypropionic acid derivative represented by formula (V)

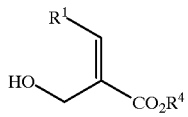

wherein $R^1$ is as defined above, and $R^4$ represents a hydrogen atom or a hydrocarbon group.

The fourth step is a step of reducing the 2-arylmethylene-3-hydroxypropionic acid derivative of formula (V) to produce a 2-arylmethyl-3-hydroxypropionic acid derivative represented by formula (VI)

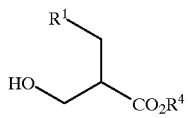

wherein $R^1$ and $R^4$ are as defined above.

The first invention includes the above-mentioned four steps in the production. If the four steps are included therein, the other steps, for example, a step of alkyl substitution, a step of rearrangement, a step of purification and the like can be added before, after, or in the middle of, these steps. When the resulting compound (VI) is an ester, a 2-arylmethyl-3-hydroxypropionic acid in the free form can easily be obtained by subjecting the ester to a usual hydrolysis step.

In the first invention, the each steps, namely any one step in the first to fourth steps and the above-mentioned hydrolysis step, which are intended for the production of the 2-arylmethyl-3-hydroxypropionic acid derivative of formula (VI) under the above mentioned first invention are also included in the present invention.

Next, the second invention is a process for producing the 2-arylmethyl-3-hydroxypropionic acid derivative ($R^4$=H) of formula (VI) in which the compound of formula (V), namely the 2-arylmethylene-3-hydroxypropionic acid derivative ($R^4$=H) is reduced in the presence of a base.

DETAILED DESCRIPTION OF THE PREFERRED EMBODIMENT

The mode of carrying out the present invention is described on the basis of, for example, the following reaction scheme showing a production route in which the first through fourth steps are conducted continuously. In this reaction scheme, $R^1$ to $R^4$ are as defined above.

Reaction Scheme

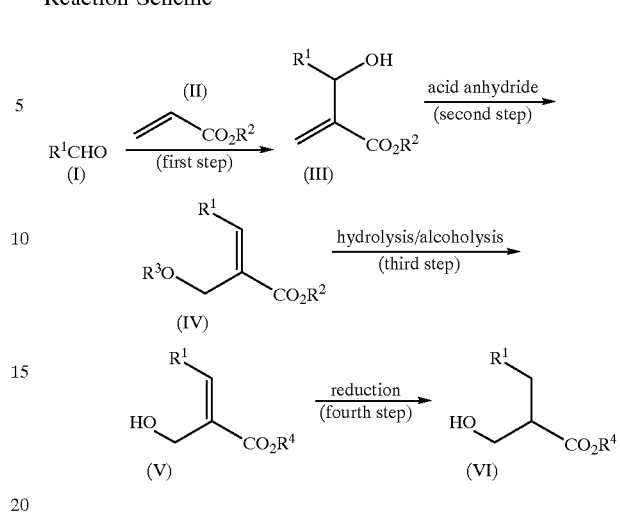

The arylaldehyde used as a starting material in the present invention (first invention) has a structure represented by formula (I).

The substituent $R^1$ bound to the formyl group in formula (I) can be an aryl group. Examples thereof include aromatic residues such as benzene, naphthalene, 4-methoxybenzene, 4-nitrobenzene and the like. The aromatic ring may be substituted unless an aromatic property is lost.

The aryl group which may be substituted has preferably from 6 to 18 carbon atoms. Specific examples of the arylaldehyde include benzaldehyde, 2-naphthylaldehyde, 4-methoxybenzaldehyde, 4-nitrobenzaldehyde and the like.

As $R^1$, a phenyl group and a naphthyl group are especially preferable, and a phenyl group is further more preferable, for reasons of simplicity.

The substituent $R^2$ in the acrylic acid ester (II) is a hydrocarbon group. It is not particularly limited if it is a hydrocarbon residue and so long as the properties for the ester are maintained. Preferable examples of this substituent include a linear or branched, saturated or unsaturated hydrocarbon group having from 1 to 5 carbon atoms, an aryl group (for example, an aromatic ring thereof may have a substituent) or a cycloalkyl group (a ring thereof may have a carbon-carbon unsaturated bond) having from 6 to 18 carbon atoms, and an aralkyl group having from 7 to 18 carbon atoms.

As $R^2$, a methyl group and an ethyl group are especially preferable for reasons of simplicity.

When the arylaldehyde (I) is reacted with the acrylic acid ester (II) to form the 3-hydroxy-2-methylene-3-arylpropionic acid ester (III), this reaction is not particularly difficult. For example, the Baylis-Hillman reaction (refer to Y. Fort, M.-C. Berthe, P. Caubere, Synth. Commun. 1992, vol. 22, 1265; P. Perlmutter, E. Puniani, G. Westman, Tetrahedron Lett. 1996, vol. 37, 1715; and S. Rafel, J. W. Leahy, J. Org. Chem. 1997, vol. 62, 1521) can be used. For example, the arylaldehyde (I) can be mixed with the acrylic acid ester (II) in the presence of diazabicyclo[2.2.2]octane for reaction. A reaction solvent is not necessarily used. A solvent which does not influence the reaction, for example, toluene, dichloromethane or tetrahydrofuran, may be used. The reaction temperature is preferably between −20 and 70° C., more preferably between 20 and 40° C. The amount of the acrylic acid ester (II) is preferably between 0.5 and 2 equivalents, more preferably between 0.8 and 1.5 equivalents based on the arylaldehyde. The amount of diazabicyclo[2.2.2]octane is preferably between 0.1 and 1.5 equivalents, more preferably between 0.1 and 0.5 equivalents based on the arylaldehyde (I).

When the 3-hydroxy-2-methylene-3-arylpropionic acid ester (III) is converted into the 2-aralkylidene-3-acyloxypropionic acid ester (IV), it can be reacted with the acid anhydride in the presence of, for example, a catalytic amount of an acid (refer to P. H. Mason, N. D. Emslie, Tetrahedron 1994, vol. 50, 12001). The acid used is not particularly limited. For example, sulfuric acid, hydrochloric acid, p-toluenesulfonic acid, methanesulfonic acid, trifluoroacetic acid, and the like are available. Examples of the acid anhydride include acetic anhydride, propionic anhydride, benzoic anhydride and the like. Two acyl groups of the acid anhydride molecule are usually the same, but they are not necessarily the same, and may be different (mixed acids anhydride). When the acyl groups are different, the compound (IV) has two kinds of different groups for the substituent group $R^3$. Thus, it is a mixture of two types. The substituent group $R^3$ is an acyl group constituting the acid anhydride used. It is not particularly limited so long as the properties for the acyl group are shown. Preferable examples of the substituent $R^3$ include a linear, branched or cyclic alkanoyl group having from 2 to 18 carbon atoms (which may contain a carbon-carbon unsaturated bond), and an arylcarbonyl group or an aralkylcarbonyl group having from 7 to 18 carbon atoms.

As $R^3$, an acetyl group is especially preferable for reasons of simplicity.

The amount of the acid anhydride used for the reaction is preferably between 1.0 and 10 equivalents, more preferably between 1.5 and 3.0 equivalents based on the compound (III). A reaction solvent is not necessarily used. A solvent which does not influence the reaction, for example, toluene, dichloromethane, tetrahydrofuran or the like, may be used. The reaction temperature is preferably between 0 and 150° C., more preferably between 50 and 100° C.

In order to convert the 2-aralkylidene-3-acyloxypropionic acid ester (IV) into the 2-aralkylidene-3-hydroxypropionic acid (formula (V), $R^4$=H), it can be subjected to hydrolysis under usual conditions for the hydrolysis reaction. For example, the 2-aralkylidene-3-hydroxypropionic acid (formula (V), $R^4$=H) can easily be obtained by dissolving the 2-aralkylidene-3-acyloxypropionic acid ester (IV) in the methanol, hydrolyzing the same in the solution with a sodium hydroxide aqueous solution, and then neutralizing the hydrolyzate with an acid. Alternatively, the 2-aralkylidene-3-hydroxypropionic acid ester (formula (V), $R^4$=hydrocarbon group) can be obtained by solvolysis (alcoholysis) to the above ester (IV) in an alcohol solvent. It is also possible that an organic acid ester which is formed as a by-product in this case is removed through concentration or the like, and then the resulting ester is further hydrolyzed to form the 2-aralkylidene-3-hydroxypropionic acid (V), or that the ester is directly reduced in the subsequent fourth step.

For the hydrolysis, not only alkali hydrolysis but also acid hydrolysis using hydrochloric acid or sulfuric acid can be used. In the hydrolysis reaction, both of the acyloxy moiety ($R^3O$ moiety) and the carboxyl moiety ($CO_2R^2$ moiety) in the compound of the formula (IV) can be hydrolyzed at one stage or at two divided stages (refer to Example 7 which will be described later).

In the hydrolysis reaction at two divided stages, each hydrolysis step is also included in the scope of the present invention so long as it is conducted to meet the object of the present invention.

In the alcoholysis, the reaction can be conducted using an alcohol represented by the formula $R^4OH$ as a solvent. $R^4$ represents a hydrocarbon group, and is the same as $R^2$ mentioned above. Examples of $R^4$ are also the same as those of $R^2$. A lower alkyl group having 5 or less carbon atoms is preferable. It is convenient to select the same group as the substituent $R^2$ in the compound (IV). In this case, a methyl group and an ethyl group are especially further more preferable for reasons of simplicity.

The alcoholysis is conducted for converting only the substituent $R^3O$ moiety in the compound of formula (IV) into the substituent HO through hydrolysis, and the substituent $CO_2R^2$ moiety is to maintain the esterified carboxyl group. Accordingly, with respect to the esterified carboxyl group to be maintained, the moiety of the alcohol residue may be maintained, exchanged or partially exchanged in the process of the present invention.

For example, the reaction can be conducted in the presence of an alkali such as sodium hydroxide using methanol or ethanol as an alcohol solvent at from 20 to 30° C. for from 1 to 10 hours.

The 2-aralkylidene-3-hydroxypropionic acid or its ester (V) can be converted into the 2-aralkyl-3-hydroxypropionic acid or its ester (VI) by subjecting the same to a reduction step, for example, catalytic hydrogenation step in the presence of a metallic catalyst. As the metallic catalyst for catalytic hydrogenation, for example, palladium, nickel, ruthenium, rhodium, platinum the like can be used. The solvent to be used is not particularly limited unless it influences the reaction. Preferable examples of the solvent include alcohol solvents such as methanol, ethanol and 2-propanol; ester solvents such as ethyl acetate and isopropyl acetate; ether solvents such as tetrahydrofuran and methyl tert-butyl ether; toluene; dimethylformamide; and water. The hydrogen pressure in the hydrogenation is preferably between 1 and 100 atm, more preferably between 1 and 5 atm. With respect to a side reaction occurring in this hydrogenation, there is a reaction in which the resulting 2-aralkyl-3-hydroxypropionic acid or its ester (VI) is dehydrated to form a 2-aralkylacrylic acid or its ester which is further reduced to form a 2-aralkylpropionic acid or its ester. For suppressing this side reaction, it has been newly found (second invention) that it is especially effective to reduce a free 2-aralkylidene-3-hydroxypropionic acid (V, $R^1$=aryl group, $R^4$=H) in the presence of a base. Preferable examples of the base include organic bases such as triethylamine and pyridine; and inorganic bases such as sodium hydroxide, potassium carbonate and ammonia. Triethylamine, trimethylamine and ammonia are especially preferable.

When the compound (V) is an ester, the free 2-aralkylidene-3-hydroxypropionic acid (formula (V), $R^1$=aryl group, $R^4$=H) can easily be formed by subjecting the ester to the ordinary hydrolysis, for example, by subjecting a methanol or ethanol solution thereof to hydrolysis with an alkaline aqueous solution of sodium hydroxide or the like at from 20 to 30° C. for from 1 to 10 hours.

For the 2-aralkylidene-3-hydroxypropionic acid (formula (V) $R^1$=aryl group, $R^4$=H) used as the starting material in the second invention, the 2-aralkylidene-3-hydroxypropionic acid (formula (V), $R^1$=aryl group, $R^4$=H) obtained in the third step of hydrolysis in the first invention can be employed. This compound can also be obtained by further hydrolyzing the ester formed in the third step of alcoholysis.

EXAMPLES

The present invention is illustrated more specifically by referring to the following Examples and Comparative Example. However, the present invention is not limited thereto.

Example 1

Synthesis of methyl 3-hydroxy-2-methylene-3-phenylpropionate [formula (III), $R^1$=Ph, $R^2$=Me]

Benzaldehyde [formula (I), $R^1$=Ph, 63.67 g (600 mmols)], 60 ml (667 mmols) of methyl acrylate [formula (II), $R^2$=Me] and 13.46 g (120 mmols) of 1,4-diazabicyclo[2,2,2]octane were mixed, and stirred at room temperature for 119 hours. After the completion of the reaction, 60 ml of water, 60 ml of 37% hydrochloric acid and 120 ml of ethyl acetate were added to the reaction solution, and the organic layer was then extracted. The resulting organic layer was washed twice with 60 ml of a saturated aqueous solution of sodium chloride, dried over anhydrous sodium sulfate, separated by filtration, and concentrated under reduced pressure to obtain 108.8 g of a crude product of the above title compound.

$^1$H-NMR (CDCl$_3$) δ: 3.12 (1H, s), 3.69 (3H, s), 5.55 (1H, s), 5.83 (1H, s), 6.33 (1H, s), 7.29–7.37 (5H, m).

Example 2

Synthesis of methyl 2-benzylidene-3-acetoxypropionate [formula (IV), $R^1$=Ph, $R^2$=Me, $R^3$=acetyl group]

Methyl 3-hydroxy-2-methylene-3-phenylpropionate [formula (III), $R^1$=Ph, $R^2$=Me, 108.8 g] obtained in Example1 was dissolved in 113 ml (1.20 mols) of acetic anhydride, and 0.2 ml of sulfuric acid were added thereto. The resulting mixture was stirred at 100° C. for 4 hours. After the completion of the reaction, the reaction solution was concentrated under reduced pressure to obtain 143.9 g of a crude product of the above title compound. The $^1$H-NMR spectrum of this product revealed that the resulting compound was a mixture of E-form and Z-form (87:13).

E-form: $^1$H-NMR (CDCl$_3$) δ: 2.09 (3H, s), 3.82 (3H, s), 4.95 (2H, s), 7.35–7.45 (5H, m), 7.98 (1H, s).

Example 3

Synthesis of 2-benzylidene-3-hydroxypropionic acid [formula (V), $R^1$=Ph, $R^4$=H]

Methyl 2-benzylidene-3-acetoxypropionate [formula (IV), $R^1$=Ph, $R^2$=Me, $R^3$=acetyl group, 143.9 g] obtained in Example 2 was dissolved in 400 ml of methanol, and an aqueous solution of 96.0 g (97%, 2.40 mols) of sodium hydroxide in 800 ml of water was added thereto. The resulting mixture was then stirred at room temperature for 90 minutes. After the completion of the reaction, the reaction solution was concentrated under reduced pressure, and methanol was distilled off. Subsequently, the residue was neutralized with the addition of 100 ml of water and 250 ml of 36% hydrochloric acid, and extracted with 600 ml of ethyl acetate. The resulting organic layer was washed with 300 ml of a saturated aqueous solution of sodium chloride, and insoluble matters were separated by filtration. The resulting solution was concentrated under reduced pressure. Toluene was added to the resulting residue in four divided portions in an amount of 250 ml each. The mixture was concentrated under reduced pressure, and acetic acid was removed to obtain 107.8 g of a crude product of the above title compound.

E-form: $^1$H-NMR (CDCl$_3$) δ: 4.53 (2H, s), 7.40–7.55 (5H, m), 7.97 (1H, s). Mass spectrum (ESI): 177.0 ((M-H)-).

Example 4

Synthesis of 2-hydroxymethyl-3-phenylpropionic acid [formula (VI), $R^1$=Ph, $R^4$=H]

2-Benzylidene-3-hydroxypropionic acid [formula (V), $R^1$=Ph, $R^4$=H, 107.8 g] obtained in Example 3 was dissolved in 500 ml of methanol, and 100 ml (717 mmols) of triethylamine and 5.00 g (water content 52.7%) of 5% palladium-carbon were then added thereto. The resulting mixture was subjected to catalytic reduction in a hydrogen atmosphere for 50 hours. After the completion of the reaction, the reaction solution was subjected to filtration with Celite to remove the palladium-carbon. The HPLC analysis of the thus-obtained filtrate revealed that the above title compound was contained in an amount of 71.0 g (394 mmols, yield based on benzaldehyde: 65.7%).

The filtrate was concentrated under reduced pressure, and the resulting residue was dissolved in 600 ml of ethyl acetate. To this were added 600 ml of water and 150 ml of 37% hydrochloric acid. The mixture obtained was stirred, and the organic layer was extracted. The resulting organic layer was washed with an aqueous solution of 37% hydrochloric acid in 240 ml of water and with 300 ml of a saturated aqueous solution of sodium chloride, and dried over anhydrous sodium sulfate. This was separated by filtration, and concentrated under reduced pressure to obtain a crude product of the above title compound. This crude product was dissolved in 150 ml of ethyl acetate, and 450 ml of hexane were added to the solution. The mixture was gradually cooled from 60° C. to 5° C. The crystals precipitated were collected by filtration, and dried to obtain 48.45 g (purity 96.5%, 259.5 mmols, yield based on benzaldehyde: 43.3%) of the above title compound.

$^1$H-NMR (CDCl$_3$) δ: 2.83–2.94 (2H, m), 3.09 (1H, m), 3.70–3.83 (2H, m), 7.20–7.33 (5H, m).

Comparative Example

Example 4 was repeated except that triethylamine was not used. As a result, 55% of the product was the above title compound, and 45% thereof was by-product 2-methyl-3-phenylpropionic acid.

Example 5

Synthesis of methyl 3-hydroxy-2-methylene-3-phenylpropionate

A mixture of 63.67 g (600 mmols) of benzaldehyde, 60 ml (667 mmols) of methyl acrylate and 13.46 g (120 mmols) of 1,4-diazabicyclo[2.2.2]octane was stirred at room temperature for 119 hours. After the completion of the reaction, 60 ml of water, 60 ml of 36% hydrochloric acid and 120 ml of ethyl acetate were added to the reaction solution, and the organic layer was extracted. The resulting organic layer was washed twice with 60 ml of a saturated aqueous solution of sodium chloride, dried over anhydrous sodium sulfate, separated by filtration, and concentrated under reduced pressure to obtain 107.9 g of a crude product of the above title compound. The HPLC analysis of the crude product revealed that this crude product contained 100.6 g (523 mmols) of the above title compound (yield: 87%).

Example 6

Synthesis of methyl 2-benzylidene-3-acetoxypropionate

Methyl 3-hydroxy-2-methylene-3-phenylpropionate (100.6 g, 523 mmols) obtained in Example 5 was dissolved in 113 ml (1.20 mols) of acetic anhydride, and 0.2 ml of sulfuric acid were added thereto. The mixture was stirred at 100° C. for 4 hours. After the completion of the reaction, the reaction solution was concentrated under reduced pressure to obtain 135.7 g of a crude product of the above title compound.

Example 7

Synthesis of 2-benzylidene-3-hydroxypropionic acid

The crude product (135.7 g) of methyl 2-benzylidene-3-acetoxypropionate obtained in Example 6 was dissolved in 600 ml of methanol, and 9.62 g (97%, 233 mmols) of sodium hydroxide were added thereto. The mixture was stirred at room temperature for 4 hours. After the completion of the reaction, the reaction solution was concentrated under reduced pressure, and methanol and methyl acetate formed were distilled off. The residue was then dissolved in 140 ml of methanol, and an aqueous solution of 38.4 g (97%, 930 mmols) of sodium hydroxide dissolved in 340 ml of water was added thereto. The mixture was stirred at room temperature for 60 minutes.

After the completion of the reaction, the reaction solution was concentrated under reduced pressure, and methanol was distilled off. Subsequently, the residue was neutralized with the addition of 100 ml of water and 124 ml of 36% hydrochloric acid, and extracted with 600 ml of ethyl acetate. The resulting organic layer was washed with 300 ml of a saturated aqueous solution of sodium chloride, and insoluble matters were separated by filtration. Then, the resulting solution was concentrated under reduced pressure to obtain 105.3 g of a crude product of the above title compound. The HPLC analysis of the crude product revealed that this crude product contained 79.96 g (449 mmols) of the above title compound (yield 85.9%, 2 stages).

Example 8

Synthesis of 2-hydroxymethyl-3-phenylpropionic acid

2-Benzylidene-3-hydroxypropionic acid (79.96 g, 449 mmols) obtained in Example 7 was dissolved in 500 ml of methanol, and 100 ml (717 mmols) of triethylamine and 5.00 g (water content 52.7%) of 5% palladium-carbon were added thereto to conduct catalytic reduction in a hydrogen atmosphere for 7 hours. After the completion of the reaction, the palladium-carbon was removed from the reaction solution through filtration with Celite. The HPLC analysis of the resulting filtrate revealed that it contained 72.3 g (401 mmols) of the above title compound (reaction yield 89.3%).

The filtrate was concentrated under reduced pressure, and the resulting residue was dissolved in 600 ml of ethyl acetate. Six-hundred milliliters of water and 150 ml of 36% hydrochloric acid were added thereto, and the mixture was stirred. Then, the organic layer was extracted. The thus-obtained organic layer was washed with an aqueous solution of 40 ml of 36% hydrochloric acid in 240 ml of water and with 300 ml of a saturated aqueous solution of sodium chloride, and dried over anhydrous sodium sulfate. The resulting product was separated by filtration, and concentrated under reduced pressure to obtain a crude product of the above title compound. This crude product was dissolved in 150 ml of ethyl acetate, and 450 ml of n-hexane were added thereto. The mixture was gradually cooled from 60° C. to 5° C. The crystals precipitated were collected by filtration, and dried to obtain 46.1 g (purity 92.0%, 235.5 mmols) of the above title compound (isolation yield 52.4%).

Example 9

Synthesis of 2-hydroxymethyl-3-phenylpropionic acid

2-Benzylidene-3-hydroxypropionic acid (490.4 mg, 2.752 mmols) was dissolved in 7 ml of methanol, and 0.5 ml of 28% aqueous ammonia and 2 ml of water were added thereto. Then, 38 mg (water content 52.7%) of 5% palladium-carbon were added thereto, and catalytic reduction was conducted in a hydrogen atmosphere for 160 minutes. After the completion of the reaction, the reaction solution was filtered with Celite to remove the palladium-carbon. The resulting filtrate was subjected to the HPLC analysis. As a result, the filtrate contained 461 mg (2.558 mmols) of the above title compound (yield 93.0%).

Example 10

Synthesis of methyl 2-benzylidene-3-hydroxypropionate [formula (V), $R^1$=Ph, $R^4$=Me]

A crude product (5.99 g, 25.57 mmols) of methyl 2-benzylidene-3-acetoxypropionate was dissolved in 26 ml of methanol, and 3.53 g (25.5 mmols) of potassium carbonate were added thereto. The mixture was stirred at room temperature for 1 hour. Insoluble matters were separated by filtration, and the resulting solution was concentrated under reduced pressure. To the resulting residue were added 30 ml of water and 40 ml of toluene to extract an organic layer. The thus-obtained organic layer was washed with 30 ml of water and with 30 ml of a saturated aqueous solution of sodium chloride, dried over anhydrous sodium sulfate, and then concentrated under reduced pressure. The resulting residue was purified through silica gel column chromatography (silica gel 100 g, mixture of hexane and ethyl acetate at a ratio of from 3:1 to 2:1) to obtain 3.02 g (15.71 mmols) of the above title compound (yield: 61.4%).

E-form: $^1$H-NMR (CDCl$_3$) δ: 2.55 (1H, br.), 3.87 (3H, s), 4.49 (2H, s), 7.37–7.48 (5H, m), 7.84 (1H, s).

Example 11

Synthesis of methyl 2-hydroxymethyl-3-phenylpropionate [formula (VI), $R^1$=Ph, $R^4$=Me]

Methyl 2-benzylidene-3-hydroxypropionate (847.2 mg, 4.408 mmols) was dissolved in 8 ml of methanol, and 21.7 mg (water content 2.7%) of 5% palladium-carbon were added thereto to conduct catalytic reduction in a hydrogen atmosphere for 140 minutes. After the completion of the reaction, the reaction solution was filtered with Celite to remove the palladium-carbon. The resulting solution was concentrated under reduced pressure to obtain 849.2 mg of a crude product of the above title compound.

$^1$H-NMR (CDCl$_3$) δ: 2.84–2.90 (2H, m), 3.03 (1H, dd), 3.69 (s, 3H), 3.70–3.78 (2H, m), 7.17–7.32 (5H, m).

Example 12

Synthesis of 2-hydroxymethyl-3-phenylpropionic acid

Methyl 2-hydroxymethyl-3-phenylpropionate [formula (VI), $R^1$=Ph, $R^4$=Me, 844 mg) obtained in Example 11 was dissolved in 5 ml of methanol, and 3.5 ml (7.00 mmols) of a sodium hydroxide aqueous solution having a concentration of 2 mols/liter were added thereto. The mixture was stirred at room temperature for 2 hours to obtain the above title compound (reaction yield: 84.8%, 2 stages). This solution was concentrated under reduced pressure, and methanol was distilled off. Subsequently, 1.5 ml of hydrochloric acid having a concentration of 6 mols/liter were added thereto, and the mixture was cooled in an ice bath. The crystals precipitated were collected by filtration to obtain 620.3 mg (purity 84.9%, 2.923 mmols, 66.7%, 2 stages) of the above title compound.

Example 13

Synthesis of methyl 2-benzylidene-3-acetoxypropionate

Methyl 3-hydroxy-2-methylene-3-phenylpropionate (1.7836 g, 9.279 mmols) was dissolved in 1.75 ml (18.55 mmols) of acetic anhydride, and 0.03 ml of sulfuric acid were added thereto. The mixture was stirred at 100° C. for 4 hours. After the completion of the reaction, the reaction solution was concentrated under reduced pressure to obtain 2.1917 g of a crude product of the above title compound.

Example 14

Synthesis of 2-hydroxymethyl-3-phenylpropionic acid

The crude product (2.1917 g) of methyl 2-benzylidene-3-acetoxypropionate obtained in Example 13 was dissolved in 15 ml of methanol, and 84 mg (97%, 2.04 mmols) of sodium hydroxide were added thereto. The mixture was stirred at room temperature for 4 hours to form methyl 2-benzylidene-3-hydroxypropionate.

To the thus-obtained reaction solution were added 36.8 mg (water content 2.7%) of 5% palladium-carbon to conduct catalytic reduction in a hydrogen atmosphere for 19 hours to convert the same into the methyl 2-hydroxymethyl-3-phenylpropionate. The reaction solution was filtered with Celite to remove the palladium-carbon. The resulting solution was concentrated under reduced pressure.

The resulting residue was dissolved in 7 ml of methanol, and 7 ml (14.0 mmols) of a sodium hydroxide aqueous solution having a concentration of 2 mols/liter were added thereto. The mixture was stirred at room temperature for 2 hours to obtain the above title compound (reaction yield 76.1%, 4 stages). This solution was concentrated under reduced pressure, and methanol was distilled off. Then, 3 ml of hydrochloric acid having a concentration of 6 mols/liter were added thereto, and the mixture was cooled in an ice bath. The crystals precipitated were collected by filtration to obtain 1.5091 g (purity 72.5%, 6.067 mmols, 65.4%, 4 stages) of the above title compound.

[Effects of the Invention]

As described above, according to the synthesis route of the present invention, the 2-aralkyl-3-hydroxypropionic acid (or its ester) which is important as an intermediate for various medications can be produced industrially safely and easily.

Especially, the presence of the base can reduce the above-mentioned 2-aralkylidene-3-hydroxypropionic acid in a high yield, and thus produce the above-mentioned intermediate in a further higher yield. Accordingly, the present invention is industrially advantageous.

What is claimed is:

1. A process for producing a propionic acid derivative comprising the following four steps, a first step of reacting an arylaldehyde represented by formula (I)

$$R^1CHO \quad (I)$$

wherein $R^1$ represents an aryl group with an acrylic acid ester represented by formula (II)

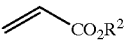

(II)

wherein $R^2$ represents a hydrocarbon group to form a 3-hydroxy-2-methylene-3-arylpropionic acid ester represented by formula (III)

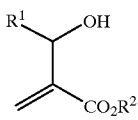

(III)

wherein $R^1$ and $R^2$ are as defined above, a second step of reacting the 3-hydroxy-2-methylene-3-arylpropionic acid ester of formula (III) with an acid anhydride to produce a 2-aralkylidene-3-acyloxypropionic acid ester represented by formula (IV)

wherein $R^1$ and $R^2$ are as defined above, and $R^3$ represents an acyl group, a third step of subjecting the 2-aralkylidene-3-acyloxypropionic acid ester of formula (IV) to hydrolysis or alcoholysis to produce a 2-arylmethylene-3-hydroxypropionic acid derivative represented by formula (V)

wherein $R^1$ is as defined above, and $R^4$ represents a hydrogen atom or a hydrocarbon group, and a fourth step of reducing the 2-arylmethylene-3-hydroxypropionic acid derivative of formula (V) to produce a 2-arylmethyl-3-hydroxypropionic acid derivative represented by formula (VI)

wherein $R^1$ and $R^4$ are as defined above.

2. The process of claim 1, wherein in the formulas, $R^1$ is a phenyl group or a naphthyl group, $R^2$ is a methyl group or an ethyl group, $R^3$ is an acetyl group, and $R^4$ is a hydrogen atom, a methyl group or an ethyl group.

3. A process comprising at least one of the steps 1 to 4 contained in the claim 1, which is intended for production of the 2-arylmethyl-3-hydroxypropionic acid derivative represented by formula (VI) in the process as defined in the claim 1:

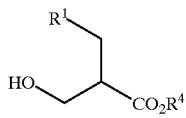
(VI)

wherein $R^1$ is an aryl group, and $R^4$ is a hydrogen atom or a hydrocarbon group.

4. A process for producing a 2-arylmethyl-3-hydroxypropionic acid derivative represented by formula (VI)

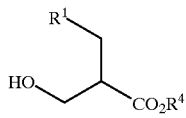
(VI)

wherein $R^1$ represents an aryl group, and $R^4$ represents a hydrogen atom, which comprises reducing a 2-arylmethylene-3-hydroxypropionic acid derivative represented by formula (V)

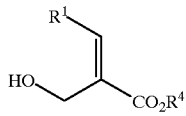
(V)

wherein $R^1$ and $R^4$ are as defined above in the presence of a base.

5. The process of claim 4, wherein said 2-arylmethylene-3-hydroxypropionic acid derivative of formula (V) is any one of a compound which is produced by subjecting a 2-aralkylidene-3-acyloxypropionic acid ester represented by formula (IV)

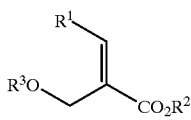
(IV)

wherein $R^1$ represents an aryl group, $R^2$ represents a hydrocarbon group, and $R^3$ represents an acyl group to hydrolysis, a compound which is produced by reacting a 3-hydroxy-2-methylene-3-arylpropionic acid ester represented by formula (III)

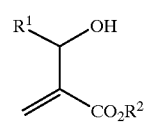
(III)

wherein $R^1$ and $R^2$ are as defined above with an acid anhydride to form the 2-aralkylidene-3-acyloxypropionic acid ester of formula (IV) and subjecting the same to hydrolysis, and a compound which is produced by reacting an arylaldehyde represented by formula (I)

$R^1CHO$ (I)

wherein $R^1$ is as defined above with an acrylic acid ester represented by formula (II)

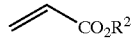
(II)

wherein $R^2$ is as defined above to form a 3-hydroxy-2-methylene-3-arylpropionic acid ester of formula (III), then reacting the same with an acid anhydride to form the 2-aralkylidene-3-acyloxypropionic acid ester of formula (IV) and subjecting the same to hydrolysis.

6. The process of claim 1, wherein in said formula (VI), $R^1$ is an aryl group and $R^4$ is a hydrocarbon group, and said 2-arylmethyl-3-hydroxypropionic acid derivative of formula (VI) is further subjected to hydrolysis to form a 2-arylmethyl-3-hydroxypropionic acid.

7. The process of claim 1, wherein in the formulas, $R^1$ is a phenyl group, and $R^4$ is a hydrogen atom.

* * * * *